United States Patent [19]

Huber

[11] 4,146,331

[45] Mar. 27, 1979

[54] ATOMIZING TUBE FOR ATOMIC ABSORPTION SPECTROMETERS

[75] Inventor: Bernhard W. Huber, Uberlingen, Fed. Rep. of Germany

[73] Assignee: Bodenseewerk Perkin-Elmer & Co., GmbH, Uberlingen, Fed. Rep. of Germany

[21] Appl. No.: 901,957

[22] Filed: May 1, 1978

Related U.S. Application Data

[63] Continuation of Ser. No. 873,581, Jan. 30, 1978, abandoned.

[30] Foreign Application Priority Data

Feb. 2, 1977 [DE] Fed. Rep. of Germany ... 7702928[U]

[51] Int. Cl.² .......................... G01N 21/16; G01J 3/30
[52] U.S. Cl. ...................................... 356/244; 356/312
[58] Field of Search .................................... 356/244, 85

[56] References Cited

U.S. PATENT DOCUMENTS

| 3,702,219 | 11/1972 | Braun et al. | 356/85 |
| 4,035,079 | 7/1977 | Sperling | 356/244 |

Primary Examiner—Vincent P. McGraw
Attorney, Agent, or Firm—Salvatore A. Giarratana; Francis L. Masselle; Edwin T. Grimes

[57] ABSTRACT

The combustion of hydrogen at the open ends of an atomic absorption spectrometer heated atomizing tube that is being supplied with substances or reagents containing volatile hydrides is eliminated by tube extensions of low heat conductive material that lower the temperature of the gas below its flash point.

5 Claims, 1 Drawing Figure

U.S. Patent      Mar. 27, 1979      4,146,331
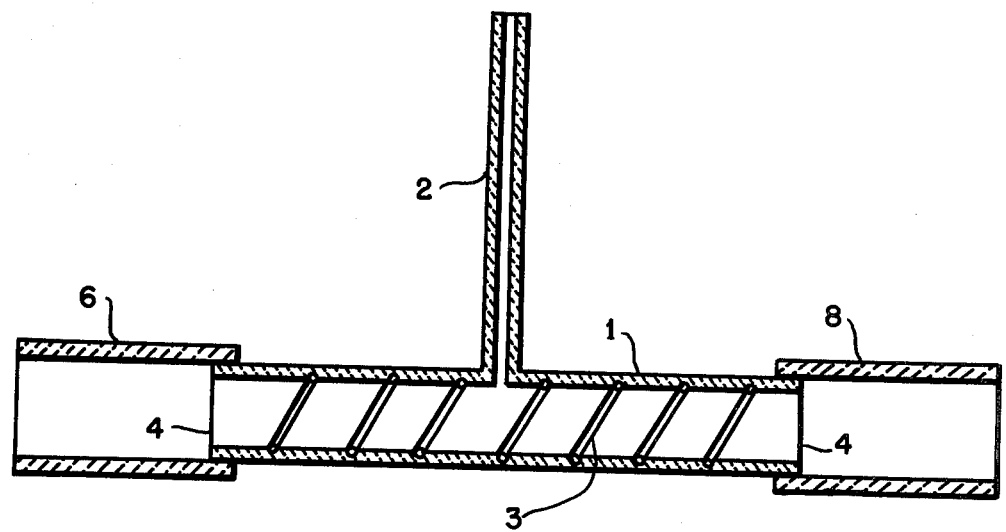

ATOMIZING TUBE FOR ATOMIC ABSORPTION SPECTROMETERS

This is a continuation of U.S. application Ser. No. 873,581, filed Jan. 30, 1978, and now abandoned.

SUMMARY OF THE INVENTION

This invention relates to atomic absorption spectrometers, and particularly to a novel improvement in the atomizing tubes for preventing ignition when high temperature hydrogen flows from the tube to contact air.

In so-called "flameless" atomic absorption measurements, samples to be analyzed are fed into the atomizing tube of an absorption spectrometer. This tube, generally formed of graphite, is mounted between annular electrodes at the end of the tube and electrical power is applied to produce a heating current that heats the tube to the desired high temperature, generally of in the range of between 800° to 1,000° C. The sample contained within the tube will then be atomized to form an atomic cloud containing each of the various elements in the sample. The measuring beam of the absorption spectrometer is then passed axially through the tube to qualitatively analyze the elements within the atomic cloud and to determine their proportional quantities by the amount of attenuation of the spectrometer beam.

Hydride generation is a well-known technique for atomic absorption spectrometric analyses of certain substances, such as those containing arsenic or selenium. Typically, suitable reagents are added to the dissolved hydride-containing substances and the combination is inserted into the center section of the heated atomizing tube where the substance is decomposed so that they appear in their atomic state. Hydrogen gas is thereby generated and, since the ends of the atomizing tube are normally open to permit the passage of the spectrometer-tested beam, the super-heated hydrogen will ignite when it drifts from the tube and contacts ambient air. The flame thus produced seriously interferes with the test being performed because it affects spectral absorption in the range below 200nm, thereby interfering with the absorption lines of such elements as arsenic (193.7nm) and selenium (196nm).

In order to effectively analyze substances containing elements having absorption lines below approximately 200nm, it is necessary to eliminate the hydrogen ignition normally occurring at the ends of the atomizing tube of an atomic absorption spectrometer.

One means for preventing hydrogen combustion includes the use of a specially designed atomizing tube having, at one end, transverse tubes through which is passed a flow of inert gas, such as argon or nitrogen. This process is determined in an article by Thompson and Thomerson in *Analyst,* September, 1974, Volume 99, at Pages 559–601. While the described technique successfully eliminates hydrogen ignition, it involves costly equipment and material not required by the present invention.

Briefly described, the atomizing tube of the present invention comprises a T-shaped tubular structure, the lateral section of which admits the specimen into the tube. The tube is heated to approximately 1,000° C. preferably by electric heating elements surrounding the central portion of the tube to thereby atomize the specimen for analysis by the spectrometer beam that passes through the tube. To prevent ignition of hydrogen when the very hot gases are released from the tube end into the atmosphere, tubular extensions of low heat conductivity material, such as graphite or quartz, are added to effectively cool the emerging gases below their flash point to thereby prevent hydrogen ignition.

DESCRIPTION OF THE DRAWING

The drawing, which illustrates a preferred embodiment of the invention, is a sectional view illustrating an atomic absorption spectrometer atomizing tube with the tube ends provided with gas-cooling extension sections.

DETAILED DESCRIPTION OF A PREFERRED EMBODIMENT

In atomic absorption spectrometric analyses, the substance to be atomized is introduced into a tubular measuring cell that is heated to a suitable level so that the substance becomes atomized. A spectrometer beam passing through the cell can then readily analyze the atomized gases by well-known spectroscopic techniques. The tested cell or atomizing tube is generally heated to a temperature of about 1,000° C. and, if the injected sample liberates hydrogen upon being atomized, the hydrogen will be ignited upon exposure to ambient air at the open ends of the atomizing tube. The flame thus produced interferes with the spectrometer test because the flames affect absorption in the range below 200nm.

It has been discovered that if the heated hydrogen is cooled to a temperature below its ignition temperature of about 500° C., it will not ignite when it comes in contact with the air upon emerging from the ends of the atomizing tube.

The drawing is a sectional view illustrating an atomizing tube with means for cooling hydrogen gases below the ignition temperature. In the drawing, atomizing tube 1 comprises an elongated tubular section having a length in the order of 10 centimeters, an outside diameter of approximately 12mm and having wall thicknesses of approximately 2mm. Located in the center of tube 1 is a lateral connector sleeve 2 through which the specimen to be anaylzed is introduced. Enveloping the cell body 1 is a heating jacket 3, preferably in the form of an electrical heating winding by which the center portion of the cell 1 may be heated to a temperature of approximately 1,000°. At such an elevated temperature, hydrogen released by atomized specimens will ignite as the hydrogen escapes from the ends 4 of the heated atomizing tube body.

To prevent such hydrogen ignition, extension tubes 6 and 8 are added to the ends 4 of the tube body 1. Extension tubes 6 and 8 are made of a heat-resistant, low heat conductivity material, such as quartz, ceramic, or graphite and have an inside diameter only slightly larger than the outside diameter of the tube 1 so that the extension tubes 6 and 8 may be slipped over the ends 4. Extension tubes 6 and 8 must be sufficiently long to adequately cool the escaping gases to a level at which hydrogen gas will not ignite. As previously mentioned, it has been found that hydrogen can be cooled to a temperature below its ignition temperature of about 500° C. It has been further found that a graphite extension tube 6, 8 that extends past the ends 4 of the tube 1 by a minimum of 24mm will provide such cooling to gases that have been heated to 1,000° C. in the center portion of the atomizing tube 1. Longer extensions, for example 32mm, provide additional cooling and are therefore preferable.

It has been found that in addition to eliminating ignition of hydrogen gases, extensions 6 and 8 being larger in diameter than the bore of the atomizing tube, prevent vignetting of the atomic absorption spectrometer test beam that is passed through the bore.

What is claimed is:

1. An atomic absorption spectrometer atomizing tube for eliminating atmosphere ignition of hot hydrogen gases released by test specimens introduced into said tube, said tube including:

an elongated tubular body open at each end, a specimen admitting tube in open communication with the central portion of said tubular body, and electrical heating means including heating wires surrounding the bore of said tubular body, the improvement comprising:

tubular extension members of low heat conductive material attached to the periphery of said body and extending beyond the ends thereof.

2. The atomizing tube claimed in claim 1 wherein said tubular extension members extend beyond the end of said tubular body by at least 24mm.

3. The atomizing tube claimed in claim 2 wherein said tubular extension members are formed of quartz.

4. The atomizing tube claimed in claim 2 wherein said extension members are formed of graphite.

5. The atomizing tube claimed in claim 2 wherein said extension members are formed of ceramic material.

UNITED STATES PATENT AND TRADEMARK OFFICE
CERTIFICATE OF CORRECTION

PATENT NO. : 4,146,331

DATED : March 27, 1979

INVENTOR(S) : Bernhard W. Huber

It is certified that error appears in the above–identified patent and that said Letters Patent are hereby corrected as shown below:

Column 1, line 55, 559-601. should read -- 595-601. --,

Signed and Sealed this

Seventh Day of August 1979

[SEAL]

Attest:

Attesting Officer

LUTRELLE F. PARKER

Acting Commissioner of Patents and Trademarks